United States Patent
Grillberger et al.

(10) Patent No.: US 10,138,461 B2
(45) Date of Patent: *Nov. 27, 2018

(54) ANIMAL PROTEIN-FREE MEDIA FOR CULTIVATION OF CELLS

(71) Applicants: Baxalta Incorporated, Bannockburn, IL (US); Baxalta GmbH, Glattpark (Opfikon) (CH)

(72) Inventors: Leopold Grillberger, Vienna (AT); Manfred Reiter, Vienna (AT); Wolfgang Mundt, Vienna (AT); Friedrich Dorner, Vienna (AT)

(73) Assignees: Baxalta Gmbh, Glattpark (Opfikon) (CH); Baxalta Incorporated, Bannockburn, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/712,408

(22) Filed: Sep. 22, 2017

(65) Prior Publication Data

US 2018/0023048 A1 Jan. 25, 2018

Related U.S. Application Data

(60) Continuation of application No. 15/598,406, filed on May 18, 2017, now Pat. No. 9,809,796, which is a continuation of application No. 14/954,705, filed on Nov. 30, 2015, now Pat. No. 9,714,411, which is a continuation of application No. 14/268,859, filed on May 2, 2014, now Pat. No. 9,222,075, which is a continuation of application No. 13/864,118, filed on Apr. 16, 2013, now Pat. No. 8,748,156, which is a continuation of application No. 12/965,111, filed on Dec. 10, 2010, now Pat. No. 8,440,408, which is a continuation of application No. 11/858,844, filed on Sep. 20, 2007, now abandoned, which is a division of application No. 10/976,399, filed on Oct. 29, 2004, now abandoned.

(51) Int. Cl.
C12N 1/20 (2006.01)
C12N 5/00 (2006.01)
C12N 5/071 (2010.01)

(52) U.S. Cl.
CPC ......... *C12N 5/0043* (2013.01); *C12N 5/0682* (2013.01); *C12N 2500/46* (2013.01); *C12N 2500/74* (2013.01); *C12N 2500/76* (2013.01); *C12N 2500/92* (2013.01)

(58) Field of Classification Search
CPC ............................ C12N 5/0043; C12N 5/0682
USPC ....................................................... 435/252.3
See application file for complete search history.

(56) References Cited

U.S. PATENT DOCUMENTS

| | | |
|---|---|---|
| 4,431,629 A | 2/1984 | Olsen |
| 4,443,540 A | 4/1984 | Chervan et al. |
| 4,767,704 A | 8/1988 | Cleveland et al. |
| 4,978,616 A | 12/1990 | Dean, Jr. et al. |
| 5,122,469 A | 6/1992 | Mather et al. |
| 5,250,421 A | 10/1993 | Kaufman et al. |
| 5,316,938 A | 5/1994 | Keen et al. |
| 5,378,612 A | 1/1995 | Nakashima et al. |
| 5,393,668 A | 2/1995 | Cinatl et al. |
| 5,441,868 A | 8/1995 | Lin |
| 5,573,937 A | 11/1996 | Shinmoto et al. |
| 5,633,162 A | 5/1997 | Keen et al. |
| 5,719,050 A | 2/1998 | Hashimoto et al. |
| 5,741,705 A | 4/1998 | Blom et al. |
| 5,789,247 A | 8/1998 | Ballay et al. |
| 5,804,420 A | 9/1998 | Chan et al. |
| 5,811,299 A | 9/1998 | Renner et al. |
| 5,840,719 A | 11/1998 | Rubin et al. |
| 5,851,800 A | 12/1998 | Adamson et al. |
| 5,885,835 A | 3/1999 | Blom et al. |
| 6,048,728 A | 4/2000 | Inlow et al. |
| 6,100,061 A | 8/2000 | Reiter et al. |
| 6,103,529 A | 8/2000 | Price et al. |
| 6,146,873 A | 11/2000 | Kistner et al. |
| 6,372,499 B1 | 4/2002 | Midoux et al. |
| 6,475,725 B1 | 11/2002 | Reiter et al. |
| 6,537,782 B1 | 3/2003 | Shibuya et al. |
| 6,596,526 B1 | 7/2003 | Plaimauer et al. |
| 6,936,441 B2 | 8/2005 | Reiter et al. |
| 7,094,574 B2 | 8/2006 | Reiter et al. |

(Continued)

FOREIGN PATENT DOCUMENTS

| | | |
|---|---|---|
| AT | 1659/99 | 9/1999 |
| AU | 78958/98 | 10/1998 |

(Continued)

OTHER PUBLICATIONS

AstraZeneca AB Opposition Brief to European Patent No. 1200561, dated Mar. 14, 2007.

(Continued)

*Primary Examiner* — Tekchand Saidha
(74) *Attorney, Agent, or Firm* — Morgan, Lewis & Bockius LLP; Christopher J. Betti; Jennifer M. Dienes

(57) ABSTRACT

The present invention relates to animal protein-free cell culture media comprising polyamines and a plant- and/or yeast-derived hydrolysate. The invention also relates to animal protein-free culturing processes, wherein cells can be cultivated, propagated and passaged without adding supplementary animal proteins in the culture medium. These processes are useful in cultivating cells, such as recombinant cells or cells infected with a virus, and for producing biological products by cell culture processes.

15 Claims, 9 Drawing Sheets

(56) References Cited

U.S. PATENT DOCUMENTS

| | | | |
|---|---|---|---|
| 7,572,619 | B2 | 8/2009 | Hauser et al. |
| 9,222,075 | B2 * | 12/2015 | Grillberger .......... C12N 5/0043 |
| 9,714,411 | B2 * | 7/2017 | Grillberger .......... C12N 5/0043 |
| 9,809,796 | B2 * | 11/2017 | Gillberger ............ C12N 5/0043 |
| 2002/0182679 | A1 | 12/2002 | Reiter et al. |
| 2003/0203448 | A1 | 10/2003 | Reiter et al. |
| 2004/0171152 | A1 | 9/2004 | Price et al. |
| 2006/0281820 | A1 | 12/2006 | Soda |

FOREIGN PATENT DOCUMENTS

| | | |
|---|---|---|
| AU | 199953636 | 3/2001 |
| CA | 2161517 | 11/1994 |
| CN | 1210866 | 3/1999 |
| EP | 0 160 457 | 11/1985 |
| EP | 0 481 791 | 4/1992 |
| EP | 0 481 792 | 4/1992 |
| EP | 0 485 689 | 5/1992 |
| EP | 0 631 731 | 1/1995 |
| EP | 0 666 312 | 8/1995 |
| EP | 0 711 835 | 5/1996 |
| EP | 0 872 487 | 10/1998 |
| EP | 0 120 896.6 | 9/2000 |
| EP | 0 121 1878 | 8/2001 |
| EP | 1 221 476 | 7/2002 |
| EP | 1 200 561 | 6/2006 |
| FR | 2 196 386 | 3/1974 |
| JP | 3-244391 | 10/1991 |
| JP | 4-316484 | 11/1992 |
| JP | 5-123178 | 5/1993 |
| JP | 06-217759 | 8/1994 |
| JP | 7-039386 | 2/1995 |
| JP | 2-859679 | 2/1999 |
| JP | H01-211488 | 8/1999 |
| JP | 2000-143619 | 5/2000 |
| JP | 2001-504344 | 4/2001 |
| KR | 2001-0026239 | 4/2001 |
| KR | 2001-0072556 | 7/2001 |
| KR | 2004-0088169 | 10/2004 |
| WO | 85/02610 | 6/1985 |
| WO | 86/04920 | 8/1986 |
| WO | 88/00967 | 2/1988 |
| WO | 89/00192 | 1/1989 |
| WO | 91/09122 | 6/1991 |
| WO | 91/10726 | 7/1991 |
| WO | 94/25599 | 11/1994 |
| WO | 96/07730 | 3/1996 |
| WO | 96/15231 | 5/1996 |
| WO | 96/18734 | 6/1996 |
| WO | 96/26266 | 8/1996 |
| WO | 96/40866 | 12/1996 |
| WO | 97/05240 | 2/1997 |
| WO | 98/08934 | 3/1998 |
| WO | 98/15614 | 4/1998 |
| WO | 98/54296 | 12/1998 |
| WO | 99/05268 | 2/1999 |
| WO | 99/47648 | 9/1999 |
| WO | 99/57246 | 11/1999 |
| WO | 00/03000 | 1/2000 |
| WO | 01/11021 | 2/2001 |
| WO | 01/14529 | 3/2001 |
| WO | 01/23527 | 4/2001 |
| WO | 02/24876 | 3/2002 |
| WO | 03/029442 | 4/2003 |
| WO | 04/005493 | 1/2004 |
| WO | 2004/073701 | 9/2004 |
| WO | 2005/035748 | 4/2005 |
| WO | 2006/026445 | 3/2006 |
| WO | 2006/045438 | 5/2006 |

OTHER PUBLICATIONS

Ballez, J. et al., "Plant protein hydrolysates support CHO-320 cells proliferation and recombinant IFN-γ production in suspension and inside microcarriers in protein-free media," Cytotechnology, vol. 44, pp. 103-114 (2004).

Bayer Healthcare AG Opposition Brief to European Patent No. 1200561, dated Mar. 13, 2007.

BD Bionutrients™; Technical Manual Advanced Bioprocessing Third Edition Revised Oct. 2006, pp. 1-67.

Berg, D.T. et al., "High-Level Expression of Secreted Proteins from Cells Adapted to Serum-Free Suspension Culture"; Bio Techniques; 1993; Vo. 14(6); pp. 972-978.

Bielicki, J. et al., "Recombinant Human Sulphamidase: Expression, Amplification, Purification and Characterization"; 1998; Biochem. J.; vol. 329; pp. 145-150.

Bioceuticals Arzneimittel AG Opposition Brief to European Patent No. 1200561, dated Mar. 14, 2007.

Biogen IDEC MA, Inc. Opposition Brief to European Patent No. 1200561, dated Mar. 14, 2007.

Brown, M.E. et al., "Process Development for the Production of Recombinant Antibodies Using the Glutamine Synthetase (GS) System"; 1992; Cytotechnology; vol. 9; pp. 231-236.

Burger, C. et al., "An Integrated Strategy for the Process Development of a Recombinant Antibody-Cytokine Fusion Protein Expressed in BHK Cells"; 1999; Appl. Microbiol. Biotechnol.; vol. 52; pp. 345-353.

Burteau, C. et al., "Fortification of a Protein-Free Cell Culture Medium with Plan Peptones Improves Cultivation and Productivity of an Interferon-γ-Producing CHO Cell Line," In Vitro Cell. Dev. Biol.—Animal, vol. 39, pp. 291-296 (Jul./Aug. 2003).

Cambrex; Classical Media Formulations, specifically MEM Product Information, 1 page.

Campina Nederland Holding B.V. Opposition Brief to European Patent No. 1220893, dated Mar. 21, 2007.

Cartier, M. and Stanners, C.P., "Stable, High-Level Expression of a Carcinoembryonic Antigen-encoding cDNA After Transfection and Amplification with eh Dominant and Selectable Asparagine Synthetase Marker"; 1990; Gene; col. 95; pp. 223-230.

Cole, E.S. et al., "Recombinant Human Thyroid Stimulating Hormone: Development of a Biotechnology Product for Detection of Metastatic Lesions of Thyroid Carcinoma"; Sep. 1993; Biotechnology; vol. 11; pp. 1014-1024.

Cruz, H.J. et al., "Adaptation of BHK Cells Producing a Recombinant Protein to Serum-Free Media and Protein-Free Medium"; 1998; Cytotechnology; vol. 26; pp. 59-64.

Declaration of Dr. Ricardo Matanguihan in support of Maxygen, Inc. Opposition Brief to European Patent No. 1220893, dated Mar. 20, 2007 (including Annexes A and B).

Declaration of Dr. Ruediger Heidemann in support of Maxygen, Inc. Opposition Brief to European Patent No. 1220893, dated Mar. 20, 2007 (including Annexes A-F).

Deltown Specialties; Peptone Selection Guide for Diagnostic and Fermentation Nutrients, 1994, 4 pages.

Donaldson, M.S. and Sculer M.L., "Low-Cost Serum-Free Medium for the BTI-Tn5B1-4 Insect Cell Line"; 1998; Biotechnol. Prog.; vol. 14; pp. 573-579.

Doyle, A. et al. eds., "Cloning," Part 4D Module 4D1 In Cell & Tissue Culture: Laboratory Procedures; 1998; John Wiley & Sons; London; Cloning Techniques (Non-hybridoma Related); pp. 4D:1.1-4D:1.9.

Eagle, H., "Amino Acid Metabolism in Mammalian Cell Cultures"; Aug. 21, 1939; Science; vol. 130; pp. 432-437.

Extract from Hauser, H. and Wagner, R. eds.; Mammalian Cell Biotechnology in Protein Production; 1997; Walter de Gruyter, Berlin; pp. 33-137.

Extract from Quest International; "Sheffield Series" Products Catalogue, 13 pages.

Farrell, P.J. et al., "High-Level Expression of Secreted Glycoproteins in Transformed Lepidopteran Insect Cells Using a Novel Expression Vector"; Dec. 20, 1998; Biotechnology and Bioengineering; vol. 60(6); pp. 656-663.

Faure, T. et al., "Stable Expression of Coagulation Factors FVIII and Fix in Recombinant Chinese Hamster Ovary Cells"; 1989; Meeting Info. 9th General Meeting of the European Society for Animal Cell Technology; Knokke (Belgium); 1988; pp. 481-488.

(56) References Cited

OTHER PUBLICATIONS

F. Hoffmann-LaRoche AG Opposition Brief to European Patent No. 1200561, dated Mar. 13, 2007.
F. Hoffmann-La Roche AG Opposition Brief to European Patent No. 1220893, dated Mar. 27, 2007.
Field, R.P. et al., "Production of a Chimeric Antibody for Tumour Imaging and Therapy From Chinese Hamster Ovary (CHO) and Myeloma Cells"; May 1990; Proceedings fo the 10th ESACT Meeting; pp. 742-744.
Fischer, B. et al., "Comparison of N-Glycan Pattern of Recombinant Human Coagulation Factors II and IX Expressed in Chinese Hamster Ovary (CHO) and African Green Monkey (Vero) Cells"; 1996; J. Thrombos. and Trombolys. ; vol. 3; pp. 57-62.
Fischer, B.E. et al., "Biochemical and Functional Characterization of Recombinant von Willebrand Factor Produced on a Large Scale"; 1997; CMLS; vol. 53; pp. 943-950.
Fischer, B.E. et al., "Structural Analysis of Recombinant von Willebrand Factor Produced at Industrial Scale Fermentation of Transformed CHO Cells Co-expressing Recombinant Furin"; 1995; FEBS Letters; vol. 375; pp. 259-262.
Fischer et al., "Structural Analysis of Recombinant von Willebrand Factor: Identification of Hetero- and Homo-Dimers"; 1994; FEBS Letters; vol. 351; pp. 345-348.
Franek, F. et al., "Plant Protein Hydrolysates: Preparation of Defined Peptide Fractions Promoting Growth and Production in Animal Cells Cultures"; 2000; Biotechnol. Prog.; vol. 16; No. 5; pp. 688-692.
Fraslon et al., "Culture of fetal alveolar epithelial type II cells in serum-free medium," In Vitro Cell Dev. Biol., 27(11) 843-852 (1991).
Freshney, R.I., "The Culture Environment: Substrate, Gas Phase, Medium, and Temperature"; Chapter 7 in Culture of Animal Cells a Manual of Basic Technique, 2nd Edition; 1987; pp. 57-84.
Friedman, J.S. et al., "High Expression in Mammalian Cells Without Amplification"; Apr. 1989; Biotechnology; vol. 7; pp. 359-362.
Gandor, C., "Amplification and Expression of Recombinant Genes in Serum-Independent Chinese Hamster Ovary Cells"; 1995; FEBS Letters; vol. 377; pp. 290-294.
Ganne et al., "Application of statistical design of experiments to the optimization of factor VIII expression by CHO cells," Cytotechnology, vol. 6, pp. 233-240 (1991).
Gibco™ Saibo bayiyo catalog (Cell culture catalog), 2003-2004, pp. 24-28, 33-36 and 43-45 (2003).
Gorfein, S.F. et al., "Recombinant Protein Production by CHO Cells Cultured in a Chemically Defined Medium"; 1996; presented at JAACT, Yokohama: Japan; 16 pages.
Haldankar, R. et al., "Stable Production of a Human Growth Hormone Antagonist From CHO Cells Adapted to Serum-Free Suspension Culture"; 1999; Biotechnol. Prog.; vol. 15(3); pp. 336-346.
Ham, R.G., "Clonal Growth of Mammalian Cells in a Chemically Defined, Synthetic Medium"; 1965; Microbiology; vol. 53; pp. 288-293.
Harant, H. et al., "Two-Dimensional Electrophoresis as a Tool for Control of Quality and Consistency in Production Systems Using Animal Cells"; 1992; Cytotechnology; vol. 8; pp. 119-127.
Harrison, S. et al., "The Manufacturing Process for Recombinant Factor IX"; Apr. 1998; Seminars in Hematology; vol. 35(2), Suppl. 2; pp. 4-10.
Hassell, T. et al., "Stability of Production of Recombinant Antibodies from Glutamine Synthetase Amplified CHO and NS0 Cell Lines"; 1992; Animal Cell Technology: Developments, Processes and Products, 11th ESACT Meeting; pp. 42-47.
Heidemann, R. et al., "The Use of Peptones as Medium Additives for High-Density Perfusion Cultures of Animal Cells"; Poster Presented at the 16th ESACT Meeting, Apr. 25-29, 199, Lugano, Switzerland; 3 pages.
Heidemann, R. et al., "The Use of Peptones as Medium Additives for the Production of a Recombinant Therapeutic Protein in High Density Perfusion Cultures of Mammalian Cells," 2000, Cytotechnology, vol. 32, pp. 157-167.
Hölttä, E. et al., "Control of Ornithine Decarboxylase in Chinese Hamster Ovary Cells by Polyamines," J. Ciol. Chem., 261(20),9502-9508 (1986).
Hsieh, C.M. et al., "The Effect of Soy Protein Hydrolyzates on Fermentation by *Lactobacillus amylovorous*"; 1999; Process Biochemistry; vol. 34; pp. 173-179.
Igarashi et al., "Polyamines: Mysterious Modulators of Cellular Functions," Biochem Biophys Res Commun, vol. 271, No. 3, pp. 559-564 (2000).
Inoue, Y. et al., "Production of Recombinant Human Monoclonal Antibody Using ras-Amplified BHK-21 Cells in a Protein-free Medium"; 1996; Biosci. Biotech. Biochem.; vol. 60(5); pp. 811-817.
Ito, Y. et al., "Protein-Free Cell Culture on an Artificial Substrate with Covalently Immobilized Insulin"; 1996; Proc. Natl. Acad. Sci. USA; vol. 93; pp. 3598-3601.
Jin, B.R. et al., "Production Kinetics and Stability of a Transfectoma Cell Line Secreting Murine/Human Chimeric Antibody"; 1993; Mol. Cells; vol. 3; pp. 233-237.
Kadouri, A. et al., "Dynamic Changes in Cytokine Secretion by Stromal Cells During Prolonged Maintenance Under Protein-Free Conditions"; 1992; International Journal of Cell Cloning; vol. 10; pp. 299-308.
Katinger, H. et al., "Long-Term Stability of Continuously Perfused Animal Cells Immobilized on Novel Macroporous Microcarriers"; 1996; Adv. Molecul. Cell Biol.; vol. 15A; pp. 193-207.
Katsuta, H. and Takaoka, T., "Amino Acid Requirements of a Substrain of StrainL Cells (Mouse Fibroblasts) in Protein-Free Chemically Defined Synthetic Media"; 1960; Japan J. Exp. Med.; vol. 30; pp. 235-259.
Katsuta, H. et al., "Effects of Polyamines on the Proliferation of Mammalian Cells in Tissue Culture"; 1975; The Japanese Journal of Experimental Medicine; vol. 45; No. 5; pp. 345-354.
Kaufman, K. et al., "Effect of von Willebrand Factor Coexpression on the Synthesis and Secretion of Factor VIII in Chinese Hamster Ovary Cells"; 1989; Molecul. Cellul. Biol.; vol. 9(3); pp. 1233-1242.
Keay, L., "Autoclavable Low Cost Serum-Free Cell Culture Media: the Growth of Established Cell Lines and Production of Viruses"; 1976; Biotechnology and Bioengineering; vol. XVIII; pp. 363-382.
Keay, L., "Autoclavable Low Cost Serum-Free Culture Media, The Growth of L Cells and BHK Cells on Peptones"; 1975; Biotechnology and Bioengineering; vol. XVII; pp. 745-764.
Keen, M.J. and Rapson, N.T., "Development of a Serum-Free Culture Medium for the Large Scale Production of Recombinant Protein From a Chinese Hamster Ovary Cell Line"; 1995; Cytotechnology; vol. 17; pp. 153-163.
Kerry Ingredients (UK) Limited Opposition Brief to European Patent No. 1220893, dated Mar. 21, 2007.
Kim, S.J. et al., "Characterization of Chimeric Antibody Producing CHO Cells in the Course of Dihydrofolate Reductase-Mediated Gene Amplification and Their Stability in the Absence of Selective Pressure"; Apr. 5, 1998; Biotechnology and Bioengineering; vol. 58(1); pp. 73-84.
Kim, N.S. et al., "Clonal Variability Within Dihydrofolate Reductase-Mediated Gene Amplified Chinese Hamster Ovary Cells: Stability in the Absence of Selective Pressure"; Dec. 20, 1998; Biotechnology and Bioengineering; vol. 60(6); pp. 679-688.
Kim et al., "Development of a Serum-Free Medium for the Production of Humanized Antibody from Chinese Hamster Ovary Cells Using a Statistical Design," In Vitro Cell Dev Biol, vol. 34, pp. 757-761 (1998).
Kwon, M.S. et al., "Use of Plant-Derived Protein Hydrolysates for Enhancing Growth of *Bombyx mori* (silkworm) Insect Cells in Suspension Culture"; 2005; Biotechnology and Applied Biochemistry; vol. 42, No. 1; pp. 1-7.
Lee, K.H. et al., "Deregulated Expression of Cloned Transcription Factor E2F-1 in Chinese Hamster Ovary Cells Shifts Protein

(56) References Cited

OTHER PUBLICATIONS

Patterns and Activates Growth in Protein-Free Medium"; 1996; Biotechnol. Bioeng.; vol. 50; pp. 273-279.
Lee et al., "The effects of various hormones and growth factors on the growth of human insulin-producing cell line in serum-free medium," Experimental and Molecular Medicine, 29(4):209-216 (1997).
Luchette, C. et al., "Isolation and Characterization of a CHO Cell Line Express rhFSH in Low Protein and Protein-Free Media"; 1997; Animal Cell Technology; pp. 669-674.
Maxygen, Inc. Opposition Brief to European Patent No. 1200561, dated Mar. 14, 2007.
Maxygen, Inc. Opposition Brief to European Patent No. 1220893, dated Mar. 20, 2007.
Merck Serono International S.A. Opposition Brief to European Patent No. 1200561, dated Mar. 12, 2007.
Merck Serono International S.A. Opposition Brief to European Patent No. 1220893, dated Mar. 20, 2007.
Merten, O.-W. et al., "Production of Influenza Virus in Serum-Free Mammalian Cell Cultures"; 1999; Dev. Biol. Stand.; vol. 98; pp. 23-37.
Merten, O.-W. et al., "The New Medium MDSS2N, Free of Any Animal Protein Supports Cell Growth and Production of Various Viruses"; 1999; Cytotechnology; vol. 30; pp. 191-201.
Merten, O.-W., "Safety Issues of Animal Products Used in Serum-Free Media"; 1999; Dev. Biol. Stand.; vol. 99; pp. 167-180.
Miao, jinmin et al., "The influences of Polymine on Protein Metabolism," 1991, Foreign Medical Sciences, vol. 13, No. 1, pp. 33-36.
Minutes of the Oral Proceedings to EP 99 939 251.7, 4 pages.
Miyaji, H. et al., "Efficient Expression of Human Beta-interferon in Namalwa KJM-1 Cells Adapted to Serum-free Medium by a dhfr Gene Coamplification Method"; 1990; Cytotechnology; vol. 4; pp. 173-180.
Miyaji, H. et al., "Expression of Human Beta-interferon in Namalwa KJM-1 Which Was Adapted to Serum-free Medium"; 1990; Cytotechnology; vol. 37; pp. 133-140.
Miyazaki et al., "Spermine enhances IgM productivity of human-human hybridoma HB4C5 cells and human peripheral blood lymphocytes," Cytotechnology, vol. 26, pp. 111-118 (1998).
Mols, J. et al., "Origin of rice protein hydrolysates added to protein-free media alters secretion and extracellular proteolysis of recombinant interferon-γ as well as CHO-320 cell growth," Biotechnology Letters, vol. 26, pp. 1043-1046 (2004).
Morgan, D., "Protein Protocols," Methods in Molecular Biology, 30 pgs., Humana Press, Totowa, NJ (1998).
Motz, M. et al., "Expression of the Epstein-Barr Virus Major Membrane Proteins in Chinese Hamster Ovary Cells"; 1986; Gene; vol. 44(2-3); pp. 353-359; Abstract, 1 page.
Müller, D., "Continuous Perfusion versus Discontinuous Fed-Batch: Production of a Cytotoxic Glycoprotein in Protein-Free CHO Suspension Cultures," Animal Cell Technology: From Target to Market, E. Lindner-Olsson et al. (eds), Proceedings of the 17th ESACT Meeting Työsand, Sweden, Jun. 10-14, 2001, pp. 293-299 (2001).
Murhammer, D.W. and Gooche, C.F., "Structural Features of Nonionic Polyglycol Polymer Molecules Responsible for the Protective Effect in Sparged Animal Cell Bioreactors"; 1990; Biotechnol. Prog.; vol. 6; pp. 142-146.
Nilsson, K. et al., "Microcarrier Culture of Recombinant Chinese Hamster Ovary Cells for Production of Human Immune Interferon and Human Tissue-Type Plasminogen Activator"; 1988; Appl. Microbiol. Biotechnol.; vol. 27; pp. 366-371.
Notice of Opposition to EP 2213724 filed by F. Hoffmann-La Roche AG, on Jun. 14, 2013, 28 pgs.
Notice of Opposition and Notice of Opposition Form to EP 2213724 filed by GE Healthcare Bio-Sciences AB, on Jun. 25, 2013, 16 pgs.
Notice of Opposition to EP 2213725 filed by F. Hoffmann-La Roche AG, on May 22, 2013, 25 pgs.
Notice of Opposition to EP 2218776 filed by F. Hoffmann-La Roche AG, on May 28, 2013, 29 pgs.
Novartis AG Opposition Brief to European Patent No. 1200561, dated Mar. 14, 2007.
Novartis AG Opposition Brief to European Patent No. 1220893, dated Mar. 21, 2007.
Novo Nordisk A/S Opposition Brief to European Patent No. 1200561, dated Mar. 14, 2007.
Novo Nordisk A/S Opposition Brief to European Patent No. 1220893, dated Mar. 21, 2007.
N.V. Organon Opposition Brief to European Patent No. 1200561, dated Mar. 14, 2007.
Nyberg, G.B. et al., "Metabolism of Peptide Amino Acids by Chinese Hamster Ovary Cells Grown in a Complex Medium"; Feb. 5, 1999; Biotechnology and Bioengineering; vol. 62(3); pp. 324-335.
Ochiai, M. et al., "Endotoxin Content in *Haemophilus influenzae* Type b Vaccine"; 2004; Jpn. J. Infect. Dis.; vol. 57; pp. 58-59.
Office Action dated Nov. 6, 2007, for U.S. Appl. No. 10/976,399.
Office Action dated Mar. 5, 2007, for U.S. Appl. No. 10/976,399.
Office Action dated Oct. 26, 2006, for U.S. Appl. No. 10/976,399.
Ogata, M. et al., "High-Level Expression of Recombinant Human Soluble Thrombomodulin in Serum-Free Medium by CHO-K1 Cells"; 1993; Appl. Microbiol. Biotechnol.; vol. 38; pp. 520-525.
Opponent's Reply to Grounds of Appeal in Opposition filed by F. Hoffmann-La Roche AG in EP 2213724 dated Feb. 8, 2016, 51 pages.
Opponent's Reply to Grounds of Appeal in Opposition filed by F. Hoffmann-La Roche AG in EP2218776 dated Feb. 8, 2016, 136 pages.
Page from the Quest International Technical Manual on Hydrolysates, 1988.
Pak, S.C.O. et al., "Super-CHO—A Cell Line Capable of Autocrine Growth Under Fully Defined Protein-Free Conditions"; 1996; Cytotechnology; vol. 22; pp. 139-146.
Pastorian et al., "Tolerance to Putrescine Toxicity in Chinese Hamster Ovary Cells is Associated with Altered Uptake and Export," Exp. Cell Res., 231:284-295 (1997).
Paterson, T. et al., "Approaches to Maximizing Stable Expression of α1-Antitrypsin in Transformed CHO Cells"; 1994; Appl. Microbiol. Biotechnol.; vol. 40; pp. 691-698.
Pu, H. et al., "Rapid Establishment of High-Producing Cell Lines Using Dicistronic Vectors with Glutamine Synthetase as the Selection Marker"; 1998; Molecular Biotechnology; vol. 10; pp. 17-25.
Qi, Y.M. et al., "Evaluation of a Simple Protein Free Medium That Supports High Levels of Monoclonal Antibody Production"; 1996; Cytotechnology; vol. 21; pp. 95-109.
Quest International; "Protein Derived Peptide Mixtures can Effectively Replace Serum, Glutamine and Other Free Amino Acids in Cell Culture Media"; Nov. 1998; Research Disclosure; pp. 1474-1476.
Quest International; Bioproducts Group HY-SOY®, Product Information, 1995, 1 page.
Quest International; Bioproducts Group HY-SOY®, Product Information, 1998, 2 pages.
Quest International; HyPep® 1510 (IPL:5Z10493) Product Information, 2 pages.
Quest International; Product Information; www.sheffield-products.com; accessed on Nov. 18, 2003; 14 pages.
Rasmussen, B. et al., "Isolation, Characterization and Recombinant Protein Expression in Veggie-CHO: A Serum-Free CHO Host Cell Line"; 1998; Cytotechnology; vol. 28; pp. 31-42.
Reiter, M. et al., "Flow Cytometry and Two-Dimensional Electrophoresis (2-DE) for System Evaluation of Long Term Continuous Perused Animal Cell Cultures in Macroporous Beads"; 1992; Cytotechnology; vol. 9; pp. 247-253.
Renner, W.A. et al., "Recombinant Cyclin E Expression Activates Proliferation andObvates Surface Attachment of Chinese Hamster Ovary (CHO) Cells in Protein-Free Medium"; Aug. 1995; Biotechnology and Bioengineering; vol. 47; pp. 476-482.
Ryll, T. et al., "Production of Recombinant Human Interleukin-2 with BHK Cells in a Hollow Fibre and a Stirred Tank Reactor with Protein-Free Medium"; 1990; Journal of Biotechnology; vol. 14; pp. 377-392.

(56) References Cited

OTHER PUBLICATIONS

SAFC Biosciences™; Dulbecco's Modified Eagle's Medium/Ham's Nutrient Mixture F12 Product Information, 2006, 2 pages.
SAFC Biosciences™; RPMI 1640 Medium Modified Product Information, 2006, 2 pages.
Scharfenberg, K. and Wagner, R., "A Reliable Strategy for the Achievement of Cell Lines Growing in Protein-Free Medium"; 1995; Animal Cell Technology: Developments towards the 21st Century; pp. 619-623.
Schlaeger, E.J., "The Protein Hydrolystate, Primatone RL, is a Cost-Effective Multiple Growth Promoter of Mammalian Cell Culture in Serum-Containing and Serum-Free Media and Displays Anti-apoptosis Properties"; 1996; Journal of Immunological Methods; vol. 194; pp. 191-199.
Schlokat, U. et al., "Herstellung und Charakterisierung von rekombinantem vonWillebrand-Faktor zur Therapeutischen Anwendyng"; 1995; 26th Hämophilie-Symposium Hamburg; pp. 147-158.
Schlokat, U. et al., "Production of Highly Homogeneous and Structurally Intact Recombinant von Willebrand Factor Multimers by Furin-Mediated Propeptide Removal in vitro"; 1996; Biotechnol. Appl. Biochem.; vol. 24; pp. 257-267.
Schneider, Y-J, "Optimisation of Hybridoma Cell Growth and Monoclonal Antibody Secretion in a Chemically Defined, Serum- and Protein-Free Culture Medium"; 1989; Journal of Immunological Methods; vol. 116; pp. 65-77.
Sigma®; Biochemicals Organic Compounds Diagnostic Reagents Catalogue, 1995, 6 pages.
Sigma-Aldrich Co. Opposition Brief to European Patent No. 1220893, dated Mar. 21, 2007.
Sinacore, M.S. et al., "CHO DUKX Cell Lineages Preadapted to Growth in Serum-Free Suspension Culture Enable Rapid Development of Cell Culture Processes for the Manufacture of Recombinant Proteins"; 1996; Biotechnol. Bioeng.; vol. 52; pp. 518-528.
Sinacore, M.S. et al., "Adaptation of Mammalian Cells to Growth in Serum-Free Media"; Molecular Biotechnology; 15: 249-257 (2000).
Stoll, T.S. et al. "Effects of Culture Conditions on the Production and Quality of Monoclonal IgA"; Aug. 15, 1997; Enzyme and Microbial Technology; vol. 21; pp. 203-211.
Sung, Y. et al., "Yeast hydrolysate as a low-cost additive to serum-free medium for the production of human thrombopoietin in suspension cultures of Chinese hamster ovary cells," Appl Microbiol Biotechnol, vol. 63, pp. 527-536 (2004).
Sunstrom, N-A. et al., "Recombinant Insulin-like Growth Factor-I (IGF-I) Production in Super-CHO Results in the Expression of IGF-I Receptor and IGF Binding Protein 3"; 1998; Cytotechnology; vol. 28; pp. 91-99.
Takashi, M. et al., "Production of Murine Monoclonal Antibodies in Protein Free Medium"; 1997; Animal Cell Technology: Basic & Applied Aspects; vol. 8; pp. 167-171.
Taylor, W.G. et al., "Studies on a Serum Substitute for Mammalian Cells in Culture. I. Biological Efficacy of Whole and Fractionated Peptone Dialysate (36086)"; 1972; Proc. Soc. Exp. Biol. Med.; vol. 139; pp. 96-99.
Tecce, M.F. and Terrana, B., "High Yield and High-Degree Purification of Human α-Fetoprotein Produced by Adaptation of the Human Hepatoma Cell Line HEP G2 in a Serum-Free Medium"; 1988; Analytical Biochemistry; vol. 169; pp. 306-311.
Technical Resources: 32500-DMEM/F-12, powder, [Retrieved from the Internet on Aug. 18, 2016], URL http://www.lifetechnologies.com/us/en/home/technical-resources/media-formulation.218.html, 3 pages.
Teige, M. et al., "Problems with Serum-Free Production of Antithrombin III Regarding Proteolytic Activity and Product Quality"; 1994; Journal of Biotechnology; vol. 34; pp. 101-105.
Tome, M.E. et al., "Consequences of aberrant ornithine decarbosylase regulation in rat hepatoma cells"; J. Cell. Physiol. 158: 237-244 (1994).
Werner, R.G. et al., "Safety and Economic Aspects of Continuous Mammalian Cell Culture"; 1992; Journal of Biotechnology; vol. 22; pp. 51-68.
Wyeth Opposition Brief to European Patent No. 1200561, dated Mar. 14, 2007.
Yamauchi, T. et al., "Production of Human Antithrombin-III in a Serum-Free Culture of CHO Cells"; 1992; Biosci. Biotech. Biochem.; vol. 56(4); pp. 600-604.
Yin, Z. et al., "Sensitivity of 3T3 Cells to Low Serum Concentration and the Association Problems of Serum Withdrawal"; 1994; Cell Biology International; vol. 18(1); pp. 39-46.
Zang, M. et al., "Production of Recombinant Proteins in Chinese Hamster Ovary Cells Using a Protein-Free Cell Culture Medium"; 1995; Biotechnology; vol. 13; pp. 389-392.
Zang-Gandor, M.O., "Improved Transfection of CHO Cells Using Endotoxin-Free Plasmid DNA"; Quiagen News; 1997; vol. 4; pp. 1, 16-18.

\* cited by examiner

| Soy Peptone Concentration (%) | FVIII Productivity (U/L/D) |
|---|---|
| 0.15 | 500 - 600 |
| 0.25 | 900 – 1,000 |
| 0.40 | 1,000 – 1,1000 |
| 0.75 | 1,000 – 1,1000 |
| 1.00 | 500 - 600 |

| Average +/- Std. Dev. | Soy Hydrolysate 0.4% | Soy Hydrolysate 0.25% | Soy Hydrolysate 0.25% + Putrescine.2HCl 1mg/L |
|---|---|---|---|
| QP [ U/L/D] | 1083 +/- 531 | 959 +/- 497 | 2190 +/- 168 |
| Qp [mU/ 10E06 cells / day] | 813 +/- 381 | 631 +/- 251 | 1473 +/- 79 |
| µ [ d$^{-1}$ ] | 0,43 +/- 0,07 | 0,40 +/- 0,13 | 0,53 +/- 0,03 |

Figure 6

|  | Putrescine [mg/L] | Average from lots |
|---|---|---|
| Quest Hy Pep 1510 total | 2.24 | n= 20 |
| DMV SE 50 MAF total | 2.41 | n= 6 |
| Quest + DMV total | 2.28 | n= 26 |

Figure 7

| Average +/- Std. Dev. | Soy Hydrolysate 0.4% | Soy Hydrolysate 0.25% + Putrescine.2HCl 1.8 mg/L |
|---|---|---|
| Volumetric Productivity QP [ mg/L/D] | 12.2 +/- 1.6 | 18.5 +/- 3.5 |
| Cell Specific Productivity qp [ µg/10E06 Cells/d] | 2.8 +/- 0.1 | 4.2 +/- 0.1 |

Figure 9

| | Qp absolute [mU/10E06 cells/ day] | Qp relative [ % ] | µ absolute [ d-1 ] | µ relative [ % ] |
|---|---|---|---|---|
| BAV –SP 0.25% no biogenic amines | 504 | 100 | 0.359 | 100 |
| BAV w/o Soy no biogenic amines | 236 | 47 | 0.299 | 83 |
| BAV –SP 0.4% no biogenic amines | 613 | 122 | 0.407 | 113 |
| BAV –SP 0.25% Putrescine.2 HCl 3.6 mg/L | 910 | 180 | 0.283 | 79 |
| BAV –SP 0.25% Putrescine.2HCl 18 mg/L | 697 | 138 | 0.305 | 85 |
| BAV –SP 0.25% Ornithine.HCl 2.5 mg/L | 657 | 130 | 0.283 | 79 |
| BAV –SP 0.25% Ornithine.HCl 12.5 mg/L | 893 | 177 | 0.299 | 83 |
| BAV –SP 0.25% Spermine.4HCl 3.4 mg/L | 752 | 149 | 0.328 | 91 |
| BAV –SP 0.25% Spermine.4HCl 17 mg/L | 1034 | 205 | 0.372 | 104 |

ANIMAL PROTEIN-FREE MEDIA FOR CULTIVATION OF CELLS

CROSS-REFERENCES TO RELATED APPLICATIONS

This application is a continuation of U.S. patent application Ser. No. 15/598,406, filed May 18, 2017; which is a continuation of U.S. patent application Ser. No. 14/954,705, filed Nov. 30, 2015, now U.S. Pat. No. 9,714,411; which is a continuation of U.S. patent application Ser. No. 14/268,859, filed May 2, 2014, now U.S. Pat. No. 9,222,075; which is a continuation of U.S. patent application Ser. No. 13/864,118, filed Apr. 16, 2013, now U.S. Pat. No. 8,748,156; which is a continuation of U.S. patent application Ser. No. 12/965,111, filed Dec. 10, 2010, now U.S. Pat. No. 8,440,408; which is a continuation of U.S. patent application Ser. No. 11/858,844, filed Sep. 20, 2007, now abandoned; which is a division of U.S. patent application Ser. No. 10/976,399, filed Oct. 29, 2004, now abandoned. Each application is herein incorporated by reference in its entirety for all purposes.

FIELD OF THE INVENTION

The present invention relates to animal protein-free cell culture media comprising a polyamine and a plant- and/or yeast-derived hydrolysate. The invention also relates to animal protein-free culturing processes, wherein cells can be cultivated, propagated and passaged without adding supplementary animal proteins in the culture medium. These processes are useful in cultivating cells, such as recombinant cells or cells infected with a virus, and for producing biological products by cell culture processes.

BACKGROUND OF THE INVENTION

For cultivation of cells, particularly eukaryotic cells, and more specifically mammalian cells, there is a constant need to use special culture media that make available the growth nutrient substances that are required for efficient growth of the cells and for the production of the proteins or viruses that are desired. For the efficient production of biological products, such as viruses or recombinant proteins, it is important that an optimal cell density is achieved as well as the protein expression itself is increased to obtain maximal product yield.

Cell culture media formulations have been supplemented with a range of additives, including undefined components like fetal calf serum (FCS), several animal derived proteins and/or protein hydrolysates of bovine origin.

In general, serum or serum-derived substances, such as albumin, transferrin or insulin, may contain unwanted agents that can contaminate the cell cultures and the biological products obtained therefrom. Furthermore, human serum derived additives have to be tested for all known viruses, including hepatitis and HIV, that can be transmitted by serum. Moreover, bovine serum and products derived therefrom bear the risk of BSE contamination. In addition, all serum-derived products can be contaminated by unknown constituents. In the case of serum or protein additives that are derived from human or other animal sources in cell culture, there are numerous problems (e.g. the varying quality in composition of the different batches and the risk of contamination with mycoplasma, viruses or BSE), particularly if the cells are used for production of drugs or vaccines for human administration.

Therefore, many attempts have been made to provide efficient host systems and cultivation conditions, which do not require serum or other animal protein compounds. Simple serum free medium typically includes basal medium, vitamins, amino acids organic or inorganic salts, and optionally additional components to make the medium nutritionally complex.

Soy hydrolysates are known to be useful for fermentation processes and can enhance the growth of many fastidious organisms, yeasts and fungi. WO 96/26266 describes that papaic digests of soy meal are a source of carbohydrate and nitrogen and many of the components can be used in tissue culture. Franek et al. (Biotechnology Progress (2000) 16, 688-692) describe growth and productivity promoting effects of defined soy hydrolysate peptide fractions.

WO 96/15231 discloses serum-free medium composed of the synthetic minimal essential medium and yeast extract for propagation of vertebrate cells and virus production process. A medium formulation composed of a basal cell culture medium comprising a rice peptide and an extract of yeast and enzymatic digest thereof, and/or a plant lipid for growth of animal cells is disclosed in WO 98/15614. A medium comprising purified soy hydrolysate for the cultivation of recombinant cells is disclosed in WO 01/23527. WO 00/03000 discloses a medium that comprises a soy hydrolysate and a yeast extract, but also requires the presence of recombinant forms of animal proteins, such as growth factors.

EP-A-0 481 791 describes a biochemically defined culture medium for culturing engineered CHO cells, which is free from protein, lipid and carbohydrate isolated from an animal source, further comprising a recombinant insulin or insulin analogue, 1% to 0.025% w/v papain digested soy peptone and putrescine. WO 98/08934 describes a serum-free eukaryotic cell culture comprising hydrolyzed soy peptides (1-1000 mg/L), 0.01 to 1 mg/L putrescine and a variety of animal-derived components, including albumin, fetuin, various hormones and other proteins. In this context, it should be also noted that putrescine is also known to be contained in standard media like DMEM/Ham's F12 in a concentration of 0.08 mg/L.

However, the media known in the state of art are often nutritionally insufficient and/or must be supplemented with animal-derived protein supplements or recombinant versions of proteins, such as insulin, insulin like growth factor or other growth factors.

Therefore, a current need exists to increase the yield of expressed recombinant protein or any other expression product, and specific growth rate of cells, and to provide an optimal cell culture medium completely free of animal proteins for production of biological products, such as those used as pharmaceuticals or vaccines in humans.

On the basis of soy peptone extracts (also designated as "soy hydrolysates") media have been developed, which do not contain animal proteins. However, the quality of commercially available lots of soy hydrolysates varies extremely and as a result, there are large variations in the production of recombinant proteins or viral products (a variation of up to a factor of 3) as a function of the lots of soy hydrolysates used ("lot-to-lot variation"). This draw back affects the proliferation of the cells as well as the protein expression of each cell.

Therefore, there is a need for an animal protein-free cell culture medium which is completely free of animal proteins and overcomes at least one of the above-mentioned problems.

SUMMARY OF THE INVENTION

An object of the present invention is to provide an animal protein-free cell culture medium which does not contain any added supplementary proteins derived from an animal source and/or recombinant animal proteins, which allows efficient cell growth and in particular protein production in a continuous quality with respect to the amount of expression per cell. A further object of the present invention is to provide a method for cultivating cells and a method for efficient expression of recombinant proteins which are free of animal proteins.

Another object of the present invention is to reduce plant and/or yeast derived hydrolysate in order to overcome inhibitory effects which would negatively impact the production yield of a desired recombinant or viral product. Hydrolysates were surprisingly found to be the cause of the lot-to-lot variations in production.

The animal protein-free cell culture medium according to the invention comprises at least one polyamine and a plant- and/or yeast-derived hydrolysate, wherein the polyamine preferably originates from a source other than the protein hydrolysate.

Surprisingly, the addition of at least one polyamine, in particular the addition of putrescine, to the animal protein-free cell culture medium provides the advantageous effect not only to promote the cell growth but in particular to increase the protein expression per cell and, in particular, recombinant protein expression per cell.

Further, the animal protein-free medium according to the present invention allows consistent cell growth and increased yield of desired products, particularly of target proteins such as recombinant proteins, independent of the quality or lot variations of the protein hydrolysate, in particular of the vegetable hydrolysates, in the animal protein-free cell culture medium. The speck supplementation of cell culture media with polyamines and a plant- and/or yeast-derived hydrolysate acts synergistically to increase cell growth, cell specific productivity and final cell density.

Therefore, the animal protein free medium according to the present invention is more favorable for recombinant protein expression and cell growth rate compared to the media known in the art. Furthermore, the animal protein-free medium according to the present invention allows the reduction of the amount of protein hydrolysate to be added to a given volume of the cell culture medium.

BRIEF DESCRIPTION OF THE DRAWINGS

FIG. 2 shows a table which compares the volumetric FVIII-CoA productivity of GD8/6 cells grown in media with different soy hydrolysate concentrations.

FIG. 5 shows a table which compares the volumetric FVIII-CoA productivity (QP [U/L/D]) and the specific growth rate ($\mu$[d–1]) of GD8/6 cells and their standard deviation grown in media with 5 different selected lots (K119-1, K138-1, M022963, M024423, M022453) of soy hydrolysates (0.4% (w/v) or 0.25% (w/v)) with the same soy hydrolysates (0.25% (w/v)) with and without putrescine.2HCl at 1 mg/L.

FIG. 6 shows a table which describes the average putrescine concentrations found in soy hydrolysates (0.4% (w/v) in cell culture medium) from different manufacturers.

FIG. 7 shows a table which compares the effect of soy hydrolysate (0.4% (w/v)) and soy hydrolysate (0.25% (w/v))+1.8 mg/L putrescine.2HCl on the volumetric productivity (QP expressed in [mg IgG1/L reactor volume/day] and cell specific productivity (qp [$\mu$g IgG 1/10E06 Cells/d]) in ARH77 cells secreting a monoclonal antibody.

FIG. 9 shows a table comparing the effect of putrescine, ornithine and spermine over a wider concentration range (0-18 mg/L) on the specific growth ($\mu$ absolute, $\mu$ relative) and the cell specific productivity (Qp absolute, Qp relative) of GD8/6 cells cultivated in BAV-medium containing 0.0% soy hydrolysate and no amines, or BAV-medium containing a reduced soy hydrolysate concentration of 0.25% supplemented with polyamines in the concentration range indicated above. BAV–SP 0.25%=BAV medium containing 0.25% soy hydrolysate; BAV–SP 0.4%=BAV medium containing 0.4% soy hydrolysate; BAV w/o soy no polyamines=BAV medium containing neither soy hydrolysate nor polyamines.

DETAILED DESCRIPTION OF THE INVENTION

Figure 1:
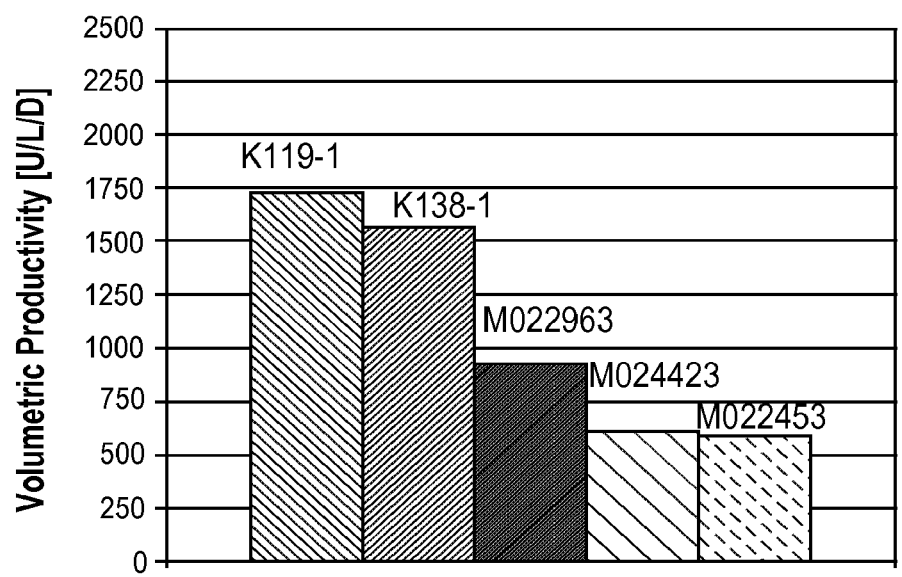
FIG. 1 shows a graph which compares (A) the volumetric FVIII-CoA productivity (expressed in [U/L/D]=FVIII COA Units per L reactor volume per day and (B) the specific growth rate ($\mu$ expressed in $[d^{-1}]$=1 per day) of GD8/6 cells as a function of the media used for culture, which were supplemented with different lots (K119-1, K138-1, M022963, M024423, M022453) of soy hydrolysates (0.4% (w/v)).
Figure 1:
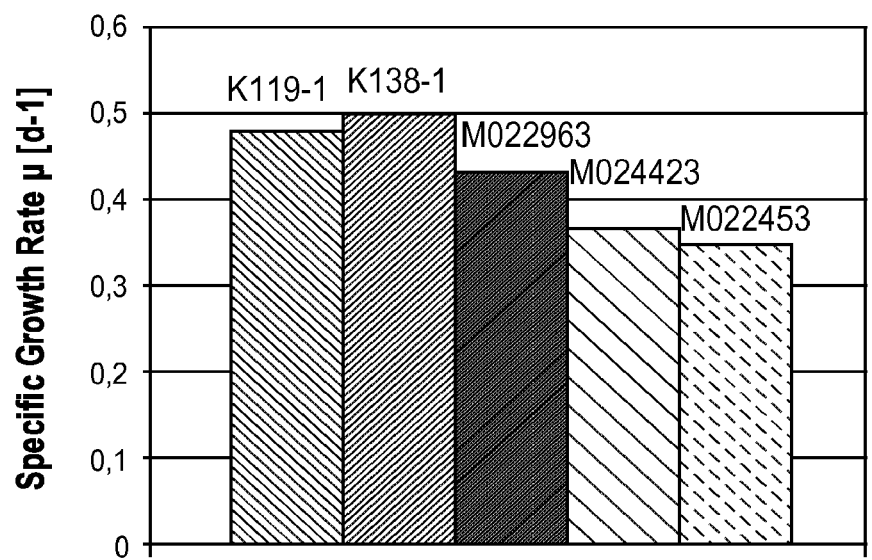
Figure 3:
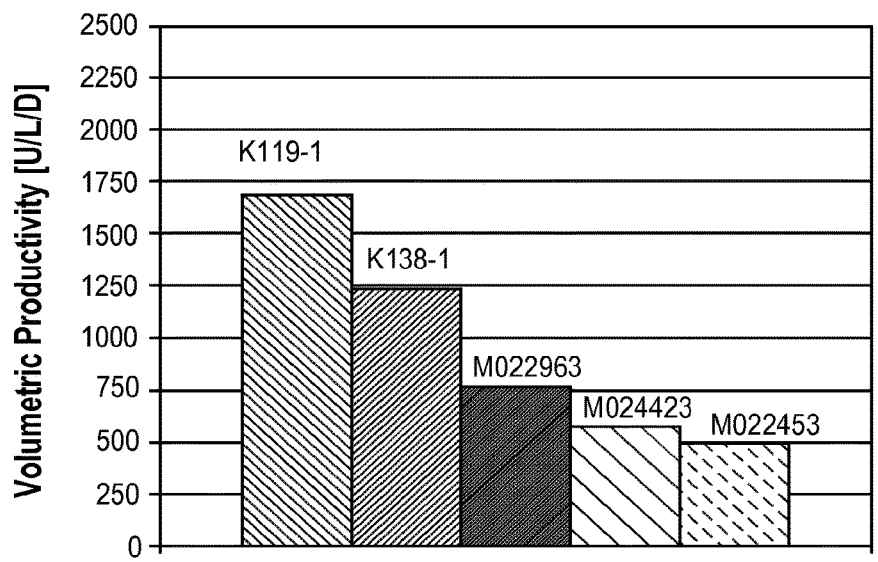
FIG. 3 shows a graph which compares the volumetric FVIII-CoA productivity of GD8/6 cells as a function of the media used for culture, which were supplemented with 5 different lots (K119-1, K138-1, M022963, M024423, M022453) of soy hydrolysates (0.25% (w/v)) (A) in the absence of putrescine and (B) in the presence of 1 mg/L putrescine.2HCl.
Figure 3:
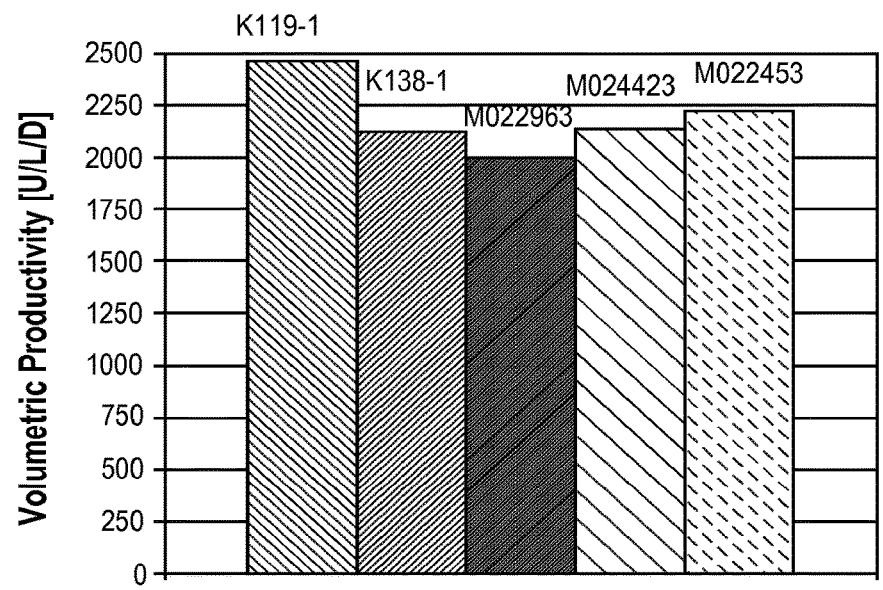

One aspect of the invention relates to an animal protein-free cell culture medium comprising at least one polyamine and a plant- and/or yeast-derived hydrolysate, in a concentration sufficiently reduced in order to avoid potential inhibitory effects of the hydrolysate.

The term "polyamine" refers to any of a group of organic compounds composed of carbon, nitrogen, and hydrogen, and containing two or more amino groups. For example, the term encompasses molecules selected from the group consisting of cadaverine, putrescine, spermidine, spermine, agmatine, and ornithine.

Unless stated differently, concentration values indicated throughout this document refer to the free base form of the component(s).

In a preferred embodiment of the animal protein-free cell culture medium the concentration of the polyamine is present in a concentration ranging from about 0.5 mg/L to about 30 mg/L, more preferably from about 0.5 mg/L to about 20 mg/L, even more preferably from about 0.5 mg/L to about 10 mg/L, more preferably from about 2 mg/L to about 8 mg/L, most preferably from about 2 to about 5 mg/L in the medium.

In a preferred embodiment the total concentration of the plant- and/or yeast-derived protein hydrolysate in the animal protein-free cell culture medium is about 0.05% to about 5% (w/v), more preferably about 0.05% to about 2% (w/v), more preferably about 0.05% to about 1% (w/v), more preferably about 0.05% to about 0.5% (w/v), most preferably about 0.05% to about 0.25% (w/v); i.e. if the medium contains a plant-and a yeast derived protein hydrolysate, the total concentration is calculated by the summing up the concentration values of each of the protein hydrolysate components contained in the medium.

The term "animal protein free cell culture medium" according to the invention refers to a medium that does not contain proteins and/or protein components from higher multicellular non-plant eukaryotes. Typical proteins that are avoided are those found in serum and serum-derived substances, such as albumin, transferrin, insulin and other growth factors. The animal protein free cell culture medium is also free of any purified animal derived products and recombinant animal derived products as well as protein digests and extracts thereof or lipid extracts or purified components thereof. Animal proteins and protein components are to be distinguished from non-animal proteins, small peptides and oligopeptides obtainable from plants (usually 10-30 amino acids in length), such as soy bean, and lower eukaryotes, such as yeast which may be included into the animal protein free cell culture medium according to the invention.

The animal protein free culture medium according to the invention may be based on any basal medium such as DMEM, Ham's F12, Medium 199, McCoy or RPMI generally known to the skilled worker. The basal medium may comprise a number of ingredients, including amino acids, vitamins, organic and inorganic salts, and sources of carbohydrate, each ingredient being present in an amount which supports the cultivation of a cell which is generally known to the person skilled in the art. The medium may contain auxiliary substances, such as buffer substances like sodium bicarbonate, antioxydants, stabilisers to counteract mechanical stress, or protease inhibitors. If required, a non-ionic surfactant such as mixtures of polyethylene glycols and polypropylene glycols (e.g. Pluronic F68®, SERVA) can be added as a defoaming agent.

The polyamine employed for the animal protein free culture medium according to the invention may be selected from the group consisting of cadaverine, putrescine, spermidine, spermine, agmatine, ornithine, and combinations thereof. Most preferably, the animal protein free culture medium contains ornithine, putrescine and spermine.

In an preferred embodiment of the animal protein free culture medium the polyamine controls DNA- and RNA-synthesis, cell proliferation, cell differentiation, membrane stabilization, and/or antioxidative DNA-protection. Putrescine, spermidine, spermine, and ornithine are examples of polyamines which exhibit these functions. Another example of a polyamine is cadaverine.

In another preferred embodiment of the animal protein-free cell culture medium according to the invention the polyamine originates from a source other than the protein hydrolysate.

In a further preferred embodiment of the animal protein-free cell culture medium the polyamine is present in a concentration ranging from about 0.5 to about 30 mg/L, more preferably from about 0.5 mg/L to about 20 mg/L, even more preferably from about 0.5 mg/L to about 10 mg/L, more preferably from about 2 mg/L to about 8 mg/L, most preferably from about 2 to about 5 mg/L in the medium, and the plant- and/or yeast-derived protein hydrolysate is present in the medium in a concentration ranging from about 0.05% to about 5% (w/v), more preferably about 0.05% to about 2% (w/v), more preferably about 0.05% to about 1% (w/v), more preferably about 0.05% to about 0.5% (w/v), most preferably about 0.05% to about 0.25% (w/v).

The plant-derived protein hydrolysate used for the animal protein-free cell culture medium according to the invention is preferably selected from the group consisting of a cereal hydrolysate and/or a soy hydrolysate. The soy hydrolysate may be a highly purified soy hydrolysate, a purified soy hydrolysate or crude soy hydrolysate.

The term "hydrolysate" includes any enzymatic digest of a vegetable or yeast extract. The "hydrolysate" can be further enzymatically digested, for example by papain, and/or formed by autolysis, thermolysis and/or plasmolysis. Hydrolysates to be used according to the present invention are also commercially available, such as HyPep 1510®, Hy-Soyo, Hy-Yeast 412® and Hi-Yeast 444®, from sources such as Quest International, Norwich, N.Y., OrganoTechnie, S.A. France, Deutsche Hefewerke GmbH, Germany, or DMV Intl. Delhi, NY. Sources of yeast extracts and soy hydrolysates are also disclosed in WO 98/15614, WO 00/03000, WO 01/23527 and U.S. Pat. No. 5,741,705.

The hydrolysates are preferably purified from crude fraction, because impurities could interfere with efficient cultivation. Purification can be carried out by ultrafiltration or Sephadex chromatography, for example with Sephadex 25 or Sephadex G10 or equivalent materials, ion exchange chromatography, affinity chromatography, size exclusion chromatography or reverse-phase-chromatography. The fractions may contain hydrolysates of defined molecular weight, preferably up to about 1000 Dalton, more preferably up to about 500 Dalton, most preferably up to about 350 Dalton. At least about 90% of the hydrolysate has preferably a molecular weight of up to about 1000 Dalton. The average molecular weight of the hydrolysates lies preferably between about 220 and about 375 Daltons. The pH value of the hydrolysate should be in the range of from about 6.5 to about 7.5. The total nitrogen content is preferably between about 5 and about 15%, and the ash content is preferably up to about 20%. The free amino acid content is preferably between about 5% and about 30%. The endotoxin content is preferably less than about 500 U/g.

The invention also provides a method of using at least one polyamine for addition to an animal protein-free cell culture medium containing a plant- and/or yeast-derived protein hydrolysate, for increasing the protein expression yield in the cultured cells. According to a preferred embodiment of the invention, the polyamine is present in the culture medium in a total concentration ranging from about 0.5 to about 30 mg/L, more preferably from about 0.5 mg/L to about 20 mg/L, even more preferably from about 0.5 mg/L to about 10 mg/L, more preferably from about 2 mg/L to about 8 mg/L, most preferably from about 2 to about 5 mg/L in the medium. Preferably, the polyamine is selected from the group consisting of cadaverine, putrescine, spermidine, spermine, agmatine, ornithine, and combinations thereof. Preferably, the plant- and/or yeast-derived protein hydrolysate is present in the medium in a concentration ranging from about 0.05% to about 5% (w/v), more preferably about 0.05% to about 2% (w/v), more preferably about 0.05% to about 1% (w/v), more preferably about 0.05% to about 0.5% (w/v), most preferably about 0.05% to about 0.25% (w/v).

The present invention further relates to a method for cultivating cells, comprising the steps of:
(a) providing an animal protein-free cell culture medium according to the invention, and
(b) propagating the cells in the medium to form a cell culture.

In a preferred embodiment the animal protein-free cell culture medium comprises at least one polyamine and a plant- and/or yeast-derived hydrolysate. Preferably the polyamine originates from a source other than the protein hydrolysate.

The present invention is not limited to any type of cells. In a preferred embodiment of the invention the cells used are for example mammalian cells, insect cells, avian cells, bacterial cells, yeast cells. The cells may be for example stem cells or recombinant cells transformed with a vector for recombinant gene expression, or cells transfected with a virus for producing viral products. The cells may also be for example cells producing a protein of interest without recombinant transformation, e.g. a B-cell producing an antibody, which may be transformed into an immortalized status e.g. by viral infection like Epstein Barr Virus infection. The cells may also be for example primary cells, e.g. chicken embryo cells, or primary cell lines. Preferred are cells that are used for in vitro virus production. In a preferred embodiment the cells may be BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, CHO cells, NS-1 cells, MRC-5 cells, WI-38 cells, BHK cells, 293 cells, RK cells, and chicken embryo cells.

The cells used according to the present invention may be cultivated by a method selected from the group of batch-cultivation, feed-batch-cultivation, perfusion cultivation and chemostate-cultivation all of which are generally known in the field.

The present invention further relates to a method for expressing a target protein such as a heterologous or autologous protein or a recombinant protein, comprising the steps of:
(a) providing a culture of cells that have been grown in an animal protein-free cell culture medium according to the invention; and
(b) introducing a nucleic acid sequence comprising a sequence coding for the target protein into the cells;
(c) selecting the cells carrying the nucleic acid sequence; and
(d) selectively inducing the expression of the target protein in the cells.

In a preferred embodiment the animal protein-free cell culture medium comprises at least one polyamine and a plant- and/or yeast-derived hydrolysate. Preferably, the polyamine originates from a source other than the protein hydrolysate.

The nucleic acid sequence comprising a sequence coding for the target protein may be a vector. The vector may be a virus or a plasmid. The sequence coding for a target protein may be a specific gene or a biological functional part thereof. In a preferred embodiment the target protein is at least a biologically active part of a blood coagulation factor such as the Factor VIII or at least a biologically active part of a protein involved in the production of red blood cells and angiogenesis such as erythropoietin, or a monoclonal antibody.

Preferably, the nucleic acid further comprises other sequences suitable for controlled expression of a target protein such as promotor sequences, as enhancers, TATA boxes, transcription initiation sites, polylinkers, restriction sites, poly-A-sequences, protein processing sequences, selection markers, and the like which are generally known to the person skilled in the art.

Most preferred are the following cell lines transformed with a recombinant vector for the expression of the respective products: CHO cells for the production of recombinant coagulation factor VIII, BHK cells for the production of recombinant erythropoietin, Epstein Barr virus transformed, immortalized human B cells for the production of human antibodies.

The present invention further relates to a method for producing a virus or part of a virus, comprising the steps of:
(a) providing a culture of cells that have been grown in an animal protein-free cell culture medium according to the invention; and
(b) infecting the cells with a virus;
(c) selecting the virus-infected cells; and
(d) incubating the cells to propagate the virus.

In a preferred embodiment the animal protein-free cell culture medium comprises at least one polyamine and a plant- and/or yeast-derived hydrolysate. More preferably, the polyamine originates from a source other than the protein hydrolysate.

The virus used in the method according to the invention may be any pathogenic virus, mammalian, preferably human virus, such as a vaccinia or attenuated vaccinia virus, e.g. for smallpox vaccines, coronavirus, preferably SARS virus, e.g. for production of SARS vaccines, orthomyoxyvirus, preferably influenza virus, e.g. for production of influenza vaccines, paramyxovirus, retrovirus, influenza A or B virus, Ross River virus, flavivirus, preferably West Nile virus or FSME virus (i.e. tick borne encephalitis virus), e.g. for the production of the respective vaccines, picornavirus, arena virus, herpesvirus, poxvirus or adenovirus.

The virus may be a wild-type-virus, an attenuated virus, a reassortant virus, or a recombinant virus or combinations thereof, e.g. attenuated and recombinant. In addition, instead of actual virions being used to infect cells with a virus, an infectious nucleic acid clone may be used. Split virions may also be used.

The method for expressing a protein or producing a virus may be used for producing immunogenic compositions comprising a virus or a virus antigen.

The cells used for the method for producing a virus may be selected from the group consisting of mammalian cells, insect cells, avian cells, bacterial cells, and yeast cells. Preferably, the cells are cultivated by a method selected from the group consisting of batch cultivation, feed-batch-cultivation, perfusion cultivation and chemostat-cultivation.

Preferred combinations of cells with viruses for producing a virus or part of a virus are Vero cell/attenuated vaccinia, Vero cellN accinia, Vero cell/Hepatitis A, Vero cell/Influenza Virus, Vero cell/West Nile Virus, Vero cell/SARS Virus, chicken embryo cells/FSME virus.

The present invention further relates to a method of using the animal protein-free cell culture medium according to the invention for culturing cells expressing a target protein.

The present invention will now be further illustrated in the following examples, without being limited thereto.

EXAMPLES

Example 1 (BAV-Medium)

Animal protein free medium was prepared with basal DMEM/HAM's F12 (1:1) medium supplemented with inorganic salts, amino acids, vitamins and other components (Life technologies, 32500 Powder). Also added were L-glutamine (600 mg/L), ascorbic acid (20 μM), ethanol amine (25 μM), the polyol detergent block-copolymer SYNPERONIC™ (SERVA) (0.25 g/L), sodium selenite (50 nM). Additionally, essential amino acids were supplemented to the cell culture medium. Further, varying concentrations of soy hydrolysate (Quest Technologies, NY or DMV Intl., N.Y.) in the range of 0.0-1.0% and varying concentrations of polyamines (0-10 mg/L) were added (FIG. 1-9).

Example 2

Cell cultures of recombinant mammalian cells (e.g. CHO-cells stably expressing Factor VIII=GD8/6-cells) were grown in suspension in a chemostat culture in 10 l bioreactors. The culture conditions of 37° C., oxygen saturation 20% and pH 7.0 to 7.1 were kept constant. The cultures were supplied with a constant feed of BAV-medium as defined in Example 1 additionally supplemented with soy hydrolysates in the range of 0.1-1.0% and/or addition of putrescine.2HCl in the range of 0-1 mg/L (cf. FIG. 1-5).

Small scale experiments with GD8/6 cells in suspension culture were carried in Techne spinner flasks at 200 ml working volume in batch refeed mode at 37° C., without pH and pO2 control. The cultures were supplied with BAV-medium as defined in Example 1 without supplementation of soy hydrolysate and polyamines, or supplemented with soy hydrolysate in the range of 0.1-0.4% and/or putrescine.2HCl, ornithine.HCl, spermine.4HCl in the range of 0-18 mg/L (equivalent to 0-10 mg/L of the polyamine without .HCl (cf. FIG. 9).

Example 3 (cf. FIGS. 1 to 5, 7, and 9)

Cell counts from suspension cells or immobilized cells were determined either by counting with a CASY® cell counter as described by Schärfe et al., (Biotechnologie in LaborPraxis 10: 1096-1103 (1988)) or by citric acid extraction and fluorescent staining of the nuclei followed by counting with a NucleoCounter® (Chemometec, DK). The specific growth rate (μ) is calculated from the increase of the cell densities ($X_t$) and/or the dilution rate (D) of the steady state of chemostat cultures of suspensions cells over a certain time interval (t): $\mu = D + \ln(X_t/X_0)/t$.

Example 4

The activity of Factor VIII (FVIII) (cf. FIGS. 1 to 5 and 9) was measured by a chromogenic assay (Chromogenic, Sweden). The activity of erythropoeitin (cf. FIG. 8) and the monoclonal antibody titer (cf. FIG. 7) were measured by ELISA test systems.

The volumetric productivity is calculated from the amount of activity units or antigen titers yielded per liter reactor volume per day (U/L/d or mg/L/d) in the respective production systems.

Figure 8:
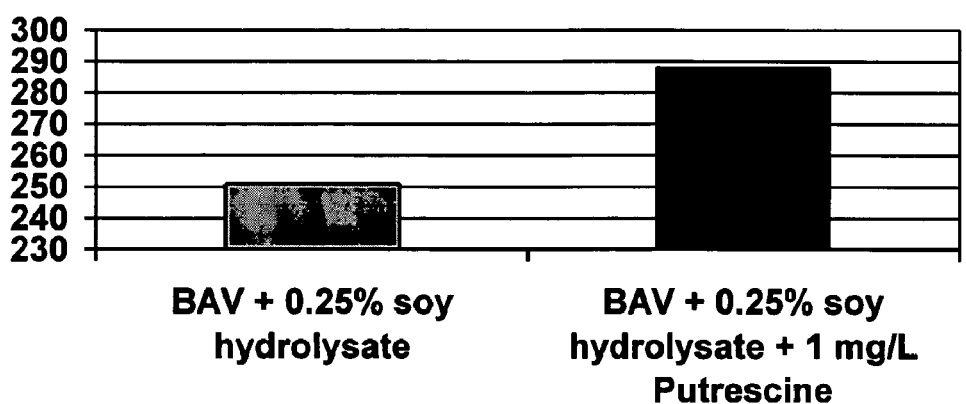
FIG. 8 shows a graph which compares the effect of soy hydrolysate (0.25% (w/v)) and soy hydrolysate (0.25% (w/v))+1 mg/L putrescine (1.8 mg/L putrescine.2HCl) on the cell specific erythropoeitin (EPO)-productivity of recombinant BHK cells (EPO production (Units)/glucose consumption (g).

The cell specific productivity is defined as the specific amount of produced protein (U or μg) per number of cells per day (cf. FIGS. 7 and 9) or as the specific amount of produced protein (U) produced per amount of D-glucose consumed by the cells (cf. FIG. 8).

Example 5

GD8/6 cells were supplied with BAV-medium containing 0.4% (w/v) of different soy hydrolysate lots. The volumetric FVIII-productivity varied from about 600 to 1800 U/L/d and the specific growth rates varied of from 0.35 to 0.52μ[d−1] between the different lots (cf. FIG. 1). This indicates that the soy hydrolysate lots at the 0.4% concentration does not allow consistent growth of the GD8/6 cells, possibly due to inhibitory substances affecting the specific growth rate (μ) which are contained in the soy hydrolysates.

Example 6

GD8/6 cells were supplied with BAV-medium containing different concentrations of soy hydrolysate lot M022257 (in the range of 0.15-1.0% w/v). The volumetric FVIII-productivity varied of from 500 to 1.100 U/L/d and reached an optimum productivity of 1.100 U/L/d at a soy hydrolysate concentration of 0.4% (w/v) (cf. FIG. 2).

Example 7

GD8/6 cells were supplied with BAV-medium containing 0.25% (w/v) of the same 5 different soy hydrolysate lots as described in Example 5 (FIGS. 3A and 4A) and 0.25% (w/v) soy hydrolysate of the same soy hydrolysate lots additionally supplemented with 1 mg/L putrescine.2 HCl (FIGS. 3B and 4B), respectively. The volumetric FVIII-productivity varied of from 1700 U/L/d to 500 U/L/d in the cells grown BAV-SP medium containing 0.25% (w/v) soy hydrolysate of different soy hydrolysate lots (FIG. 3A). The specific growth rate varied of from 0.58 to 0.24μ[d−1], indicating that the reduction of the soy hydrolysate concentration does not lead to an improved or more consistent growth rate of the cells (FIG. 4A).

In contrast, only minor variations of the volumetric FVIII-productivity (FIG. 3B) and specific growth rates (FIG. 4B) between the same soy hydrolysate lots are observed in the cells grown BAV-medium containing 0.25% (w/v) soy hydrolysate when supplemented with 1 mg/L putrescine.2HCl. The addition of 1 mg/L putrescine.2HCl approximately compensates the reduction of this polyamine by the reduction of soy hydrolysate concentration from 0.4% (w/v) to 0.25% (w/v). From this it can be concluded that not the concentration of the polyamine itself, but the addition of the polyamine in combination with the reduction of the soy hydrolysate concentrations leads to a reduction of inhibitory substances which reduce growth and productivity (see Example 5). Furthermore, the addition of putrescine also leads to an over proportional increased volumetric productivity of FVIII due to an increase of the cell specific FVIII productivity (FIG. 5).

Thus addition of putrescine to animal protein-free cell culture media not only promotes protein expression rate of cultured cells but it also reduces the amount of plant hydrolysate to be included into the culture media in order to obtain the same cell growth. As a result, culture media become less affected by the lot-by-lot variation of quality of plant hydrolysate and thus an overall improvement of the cell culture conditions is achieved.

Example 8

Figure 4:
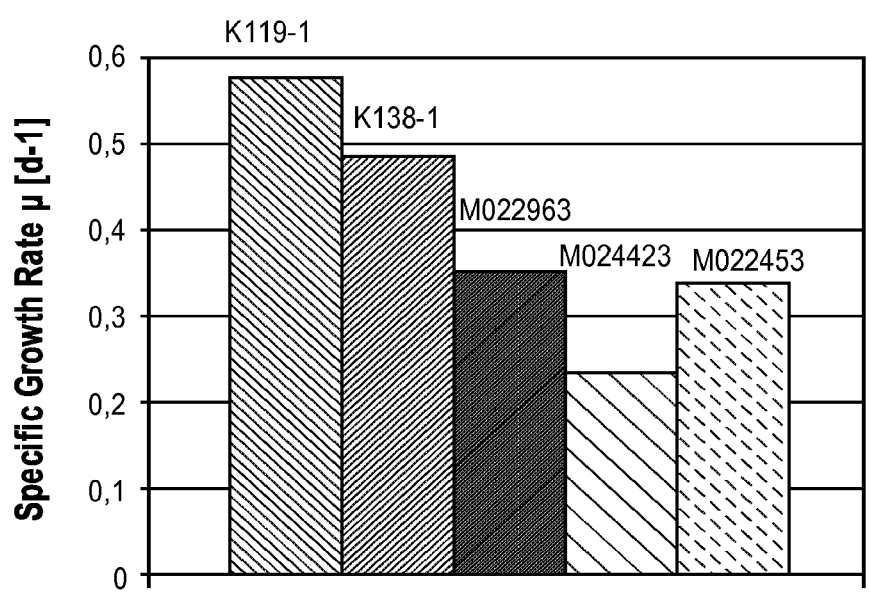
FIG. 4 shows a graph which compares the specific growth rates of GD8/6 cells as a function of the media used for culture, which were supplemented with 5 different lots (K119-1, K138-1, M22963, M024423, M022453) of soy hydrolysates (0.25% (w/v)) (A) in the absence of putrescine and (B) in the presence of 1 mg/L putrescine.2HCl.
Figure 4:
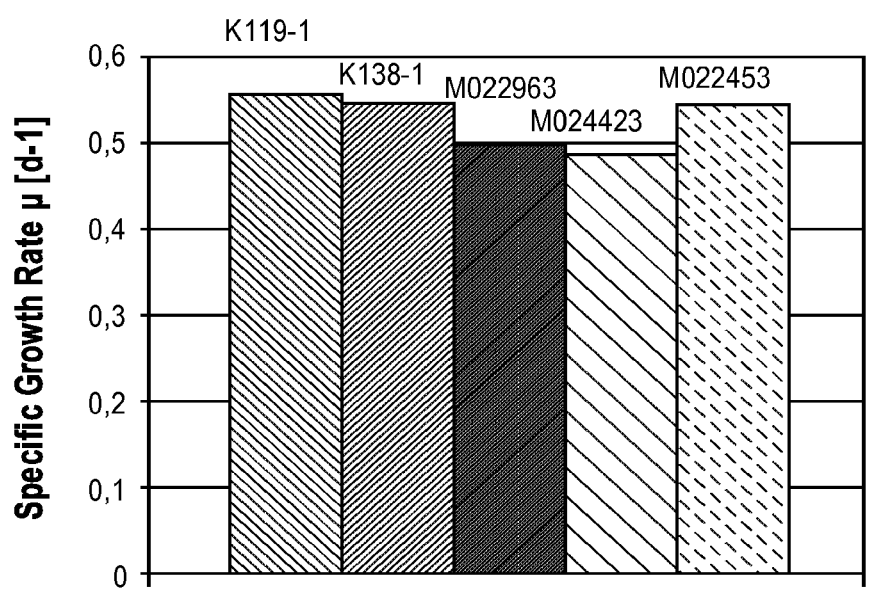

FIG. 5 comprises the statistical analysis of the Examples shown in FIGS. 1, 2 and 4: GD8/6 cells were supplied with BAV-medium containing 0.4% (w/v) of soy hydrolysate or 0.25% (w/v) soy hydrolysate or 0.25% (w/v) soy hydrolysate and 1 mg/L putrescine.2HCl. Standard deviations are calculated based on five selected lots of soy hydrolysates (K119-1, K138-1, M022963, M024423, M022453). The volumetric and cell specific FVIII-productivity and the specific growth rate with 0.25% (w/v) soy hydrolysate was lower than with 0.4% (w/v) soy hydrolysate, which confirms the optimum depicted in FIG. 2. However, the volumetric and cell specific FVIII-productivity and the specific growth rate increases in cell culture medium containing 0.25% (w/v) soy hydrolysate+1 mg/L putrescine.2HCl. Further, the standard deviation calculated from five different lots of soy hydrolysates is significantly reduced (cf. FIG. 5 [QP [U/L/D]=volumetric productivity; qp [mU/$10^6$ cells/day]=cell specific productivity).

Example 9

Examples 7 and 8 show that putrescine is an active compound supporting cell growth and, more specifically protein expression. Therefore, the concentration of putrescine from different soy hydrolysate lots from 2 different suppliers (Quest and DMV) were quantitatively analysed by a HPLC method and evaluated statistically. The concentration in the cell culture media prepared with soy hydrolysate from both suppliers was approximately 2.3 mg/L putrescine, when soy hydrolysate was added to the medium in a concentration of 0.4% (w/v) (cf. FIG. 6).

Example 10

ARH77 cells (human lymphoblastoid cell line stably expressing hIgG) were grown in a perfusion culture after immobilization on macroporous microcarriers in a 80 L stirred tank bioreactor at 37° C., pH 7.0-7.2 and pO2 20-80% air saturation, supplied with BAV medium containing 0.4% (w/v) of soy hydrolysate or 0.25% (w/v) soy hydrolysate+1.8 mg/L putrescine.2HCl. Arithmetic means and standard deviations were calculated from data points representing the steady states for the respective medium formulations. The volumetric hIgG-volumetric productivity/cell specific productivity in BAV-medium supplemented with 0.4% (w/v) soy hydrolysate was lower than in BAV-medium supplemented with 0.25% (w/v) soy hydrolysate+1.8 mg/L putrescine.2HCl. This experiment indicates that the medium composition according to the present invention is capable to promote also the expression of monoclonal antibodies from a transformed cell line. Further, the specific medium composition can also be used in perfusion cultures (cf. FIG. 7).

Example 11

Recombinant BHK cells were grown to confluence in 5% (v/v) fetal calf serum containing medium. The cells were washed with protein-free medium and incubated for 3 days in BAV medium supplemented with 0.25% (w/v) soy hydrolysate or 0.25% (w/v) soy hydrolysate+1.8 mg/L putrescine.2HCl (FIG. 8). Since no cell counting in this experiment was performed, the glucose consumption rate (g/L) was measured over three days to prove equivalent biomass in the culture system. The EPO-activity (mU/ml) was correlated with the glucose consumption rate (g/L) over three days. The addition of putrescine gives a 16% increase in EPO productivity compared to BAV-medium merely supplemented with 0.25% (w/v) soy peptone. This experiment also indicates that the medium composition according to the present invention is capable to promote the expression of different recombinant proteins.

Example 12

To prove the specific effect of putrescine, ornithine and spermine over a wider concentration range (0-18 mg/L equivalent to 0-10 mg/L of the polyamine without —.HCl) an experiment was carried where the GD8/6 cells were incubated in Techne spinner flasks at 1-1.5 E06 cells/ml in BAV-medium containing 0.25% and 0.4% soy hydrolysate without polyamines, and BA V-medium containing the reduced soy hydrolysate concentration of 0.25% with the polyamines in the above mentioned concentration range. All three polyamines in the investigated concentration range resulted in a significant increase of cell specific productivity (expressed in mU/106 cells/day) compared to the unsupplemented medium formulation with 0.25% soy hydrolysate, or the increased concentration of 0.4%. The increase of the cell specific productivity is clearly not correlating with an increased specific growth rate, which confirms the specific effect on the expression rate of recombinant FVIII of the GD8/6 cells (FIG. 9).

What is claimed is:

1. An animal protein-free cell culture medium, comprising at least one polyamine and at least one protein hydrolysate derived from the group consisting of plants and yeast, wherein the polyamine is present in the culture medium in a concentration ranging from about 0.5 to about 30 mg/L.

2. The animal protein-free cell culture medium according to claim 1, wherein the polyamine is selected from the group consisting of cadaverine, putrescine, spermidine, spermine, agmatine, ornithine, and a combination thereof.

3. The animal protein-free cell culture medium according to claim 1, wherein the polyamine is putrescine in a concentration ranging from about 0.5 to about 10 mg/L, and the protein hydrolysate is soy hydrolysate in a concentration ranging from about 0.05% (w/v) to about 5% (w/v).

4. The animal protein-free cell culture medium according to claim 1, wherein the polyamine originates from a source other than a protein hydrolysate.

5. The animal protein-free cell culture medium according to claim 1, wherein the polyamine is present in the culture medium in a concentration ranging from about 0.5 to about 10 mg/L.

6. The animal protein-free cell culture medium according to claim 1, wherein the polyamine is present in the culture medium in a concentration ranging from about 2 to about 8 mg/L.

7. The animal protein-free cell culture medium according to claim 1, wherein the protein hydrolysate is present in the culture medium in a total concentration ranging from about 0.05% (w/v) to about 5% (w/v) for all protein hydrolysates.

8. The animal protein-free cell culture medium according to claim 1, wherein the protein hydrolysate is derived from a plant selected from the group consisting cereals and soy.

9. A method for cultivating cells, comprising the steps of:
(a) providing an animal protein-free cell culture medium according to claim 1, and
(b) propagating the cells in the medium to form a cell culture.

10. The method according to claim 9, wherein the cells are selected from the group consisting of mammalian cells, insect cells, avian cells, bacterial cells, and yeast cells.

11. The method according to claim 9, wherein the cells are cultivated by a method selected from the group consisting of batch-cultivation, feed-batch-cultivation, perfusion cultivation, and chemostat-cultivation.

12. A method for expressing a target protein, comprising the steps of:
a) providing a culture of cells that have been grown in an animal protein-free cell culture medium according to claim 1;

b) introducing a nucleic acid sequence comprising a sequence coding for the target protein into the cells;
c) selecting the cells carrying the nucleic acid sequence; and
d) selectively inducing the expression of the target protein in the cells.

13. The method according to claim 12, wherein the cells are selected from the group consisting of mammalian cells, insect cells, avian cells, bacterial cells, and yeast cells.

14. The method according to claim 1 wherein the cell/target protein combination is selected from the group consisting of CHO cells/coagulation factor VIII, BHK cells/erythropoietin, Epstein Barr virus transformed, immortalized human B cells/human antibodies.

15. The method according to claim 12, wherein the cells are cultivated by a method selected from the group consisting of batch-cultivation, feed-batch-cultivation, perfusion cultivation, and chemostat-cultivation.

* * * * *

UNITED STATES PATENT AND TRADEMARK OFFICE
CERTIFICATE OF CORRECTION

PATENT NO. : 10,138,461 B2
APPLICATION NO. : 15/712408
DATED : November 27, 2018
INVENTOR(S) : Grillberger et al.

Page 1 of 1

It is certified that error appears in the above-identified patent and that said Letters Patent is hereby corrected as shown below:

On the Title Page

At item (71) Applicant: the name of the city for Baxalta GmbH should be "Zug (CH);"

In the Claims

Column 13, Line 10 (Claim 14), replace "claim 1" with --claim 12--

Signed and Sealed this
Nineteenth Day of February, 2019

Andrei Iancu
*Director of the United States Patent and Trademark Office*